United States Patent
Williams

(10) Patent No.: US 6,641,567 B1
(45) Date of Patent: Nov. 4, 2003

(54) INCONTINENCE DIAPER AND RECEPTACLE APPARATUS

(76) Inventor: Maryjane Williams, 25 Galton La., Willingboro, NJ (US) 08046

( * ) Notice: Subject to any disclaimer, the term of this patent is extended or adjusted under 35 U.S.C. 154(b) by 4 days.

(21) Appl. No.: 10/053,918

(22) Filed: Jan. 24, 2002

(51) Int. Cl.[7] .............................................. A61F 13/15
(52) U.S. Cl. ...................................... 604/327; 604/355
(58) Field of Search ................................. 604/317, 327, 604/346, 348, 351, 353, 355, 385.01, 385.09, 385.31

(56) References Cited

U.S. PATENT DOCUMENTS

| | | | | |
|---|---|---|---|---|
| 2,749,558 A | * | 6/1956 | Lent et al. ...................... 4/454 |
| 3,626,941 A | * | 12/1971 | Webb ........................... 604/291 |
| 3,751,727 A | * | 8/1973 | Shepard et al. ................ 2/2.14 |
| 3,838,691 A | * | 10/1974 | Paludan et al. .............. 604/323 |
| 4,631,061 A | * | 12/1986 | Martin ......................... 604/318 |
| 4,673,401 A | * | 6/1987 | Jensen et al. ................ 604/353 |
| 4,747,166 A | * | 5/1988 | Kuntz .......................... 4/144.1 |
| 4,791,686 A | * | 12/1988 | Taniguchi et al. ............. 4/448 |
| 4,886,508 A | * | 12/1989 | Washington ................ 604/327 |
| 4,982,462 A | * | 1/1991 | Wada ............................ 4/546 |
| 5,342,583 A | * | 8/1994 | Son ........................... 422/107 |
| 5,462,539 A | * | 10/1995 | Herman et al. ......... 604/385.25 |
| 5,678,564 A | * | 10/1997 | Lawrence et al. ........... 600/574 |
| 5,681,297 A | * | 10/1997 | Hashimoto et al. .......... 604/355 |
| 5,792,132 A | * | 8/1998 | Garcia .................... 604/385.01 |
| 5,911,222 A | * | 6/1999 | Lawrence et al. ........... 600/574 |
| 6,191,055 B1 | * | 2/2001 | Boyer et al. ................... 442/80 |
| 6,394,988 B1 | * | 5/2002 | Hashimoto ................... 604/355 |
| 6,425,889 B1 | * | 7/2002 | Kitaoka et al. ......... 604/385.01 |
| 6,443,939 B1 | * | 9/2002 | Oki et al. .................... 604/393 |

FOREIGN PATENT DOCUMENTS

WO WO 93/07839 * 4/1993 ........... A61F/5/451

* cited by examiner

Primary Examiner—Weilun Lo
Assistant Examiner—Michael Bogart

(57) ABSTRACT

An incontinence diaper and receptacle apparatus for effective and efficient collection of bodily waste after administration of an enema. The incontinence diaper and receptacle apparatus includes a diaper member which includes a sheet of material and at least one inner absorbent liner being attached to the sheet of material; and also includes an assembly for fastening the diaper member about a person's midsection; and further includes a hose being in fluid communication with the diaper member; also includes a container being connected to the hose for receiving a person's bodily waste; and further includes a diaper lift member being attached to the diaper member for lifting the diaper member to facilitate flow of the person's waste through the hose.

2 Claims, 4 Drawing Sheets

INCONTINENCE DIAPER AND RECEPTACLE APPARATUS

BACKGROUND OF THE INVENTION

1. Field of the Invention

The present invention relates to diapers and human waste receptacles and more particularly pertains to a new incontinence diaper and receptacle apparatus for effective and efficient collection of bodily waste after administration of an enema.

2. Description of the Prior Art

The use of diapers and human waste receptacles is known in the prior art. More specifically, diapers and human waste receptacles heretofore devised and utilized are known to consist basically of familiar, expected and obvious structural configurations, notwithstanding the various designs described by the crowded prior art which have been developed for the fulfillment of countless objectives and requirements.

Known prior art includes U.S. Pat. No. 5,792,132; U.S. Pat. No. 5,049,144; U.S. Pat. No. 4,813,943; U.S. Pat. No. 5,678,564; U.S. Pat. No. Des. 288,485; and U.S. Pat. No. 3,194,238.

While these devices fulfill their respective, particular objectives and requirements, the aforementioned patents do not disclose a new incontinence diaper and receptacle apparatus. The prior art describes diapers worn about the user's midsection.

SUMMARY OF THE INVENTION

The general purpose of the present invention, which will be described subsequently in greater detail, is to provide a new incontinence diaper and receptacle apparatus which has many of the advantages of the diapers and human waste receptacles mentioned heretofore and many novel features that result in a new incontinence diaper and receptacle apparatus which is not anticipated, rendered obvious, suggested, or even implied by any of the prior art diapers and human waste receptacles, either alone or in any combination thereof. The inventive device includes a diaper member which includes a sheet of material and at least one inner absorbent liner being attached to the sheet of material; and also includes an assembly for fastening the diaper member about a person's midsection; and further includes a hose being in fluid communication with the diaper member; also includes a container being connected to the hose for receiving a person's bodily waste; and further includes a diaper lift member being attached to the diaper member for lifting the diaper member to facilitate flow of the person's waste through the hose. The inventive device keeps the diaper member correctly positioned about the person's midsection so that the bodily waste is drained through the hose to the container without a messy buildup in the diaper member.

There has thus been outlined, rather broadly, the more important features of the incontinence diaper and receptacle apparatus in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new incontinence diaper and receptacle apparatus which has many of the advantages of the diapers and human waste receptacles mentioned heretofore and many novel features that result in a new incontinence diaper and receptacle apparatus which is not anticipated, rendered obvious, suggested, or even implied by any of the prior art diapers and human waste receptacles, either alone or in any combination thereof.

Still another object of the present invention is to provide a new incontinence diaper and receptacle apparatus for effective and efficient collection of bodily waste after administration of an enema.

Still yet another object of the present invention is to provide a new incontinence diaper and receptacle apparatus that is easy and convenient to put on.

Even still another object of the present invention is to provide a new incontinence diaper and receptacle apparatus that remains in a position to effectively drain the bodily waste from the diaper member to the container without any worry of a buildup in the diaper member.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
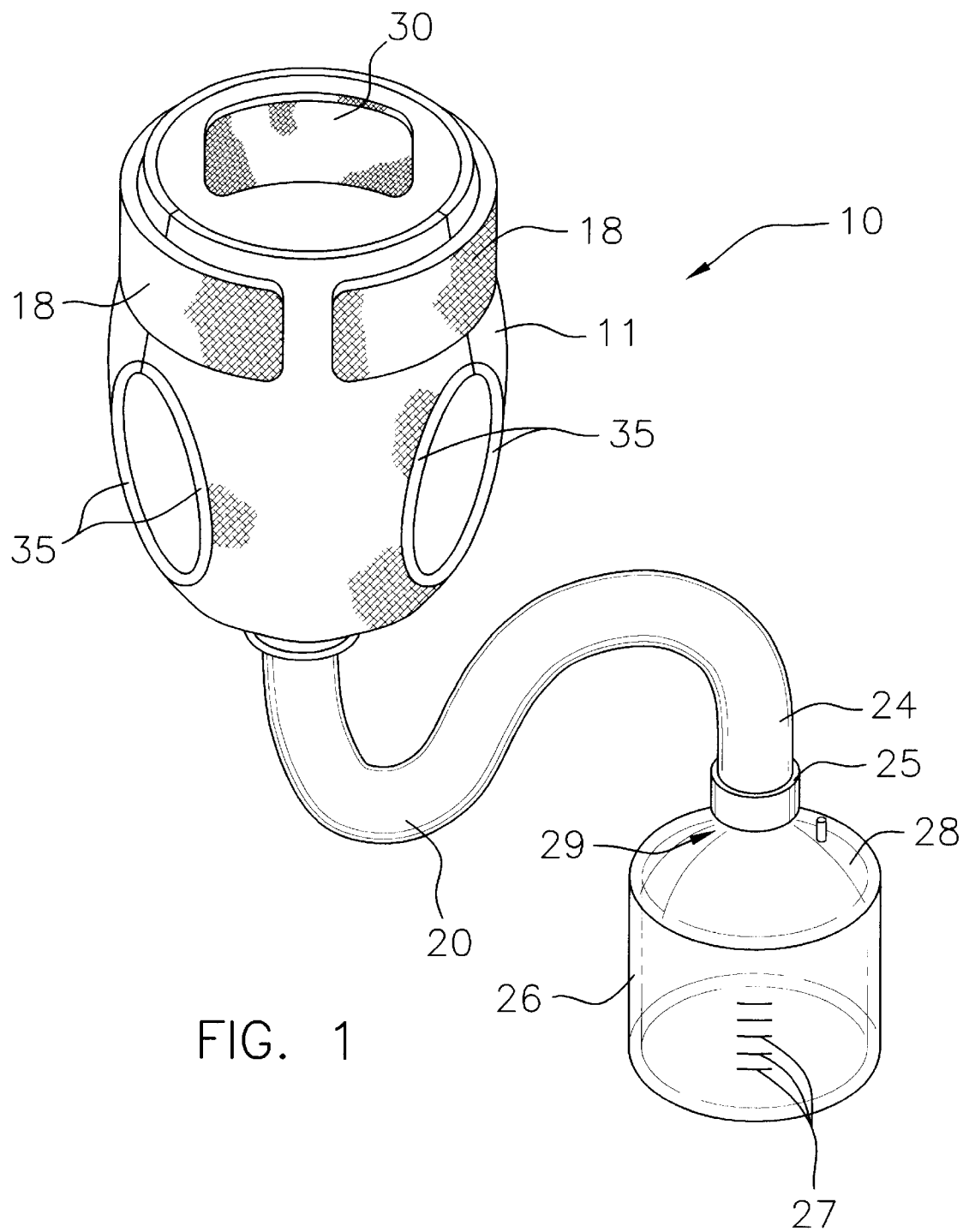
FIG. 1 is a perspective view of a new incontinence diaper and receptacle apparatus according to the present invention.
Figure 2:
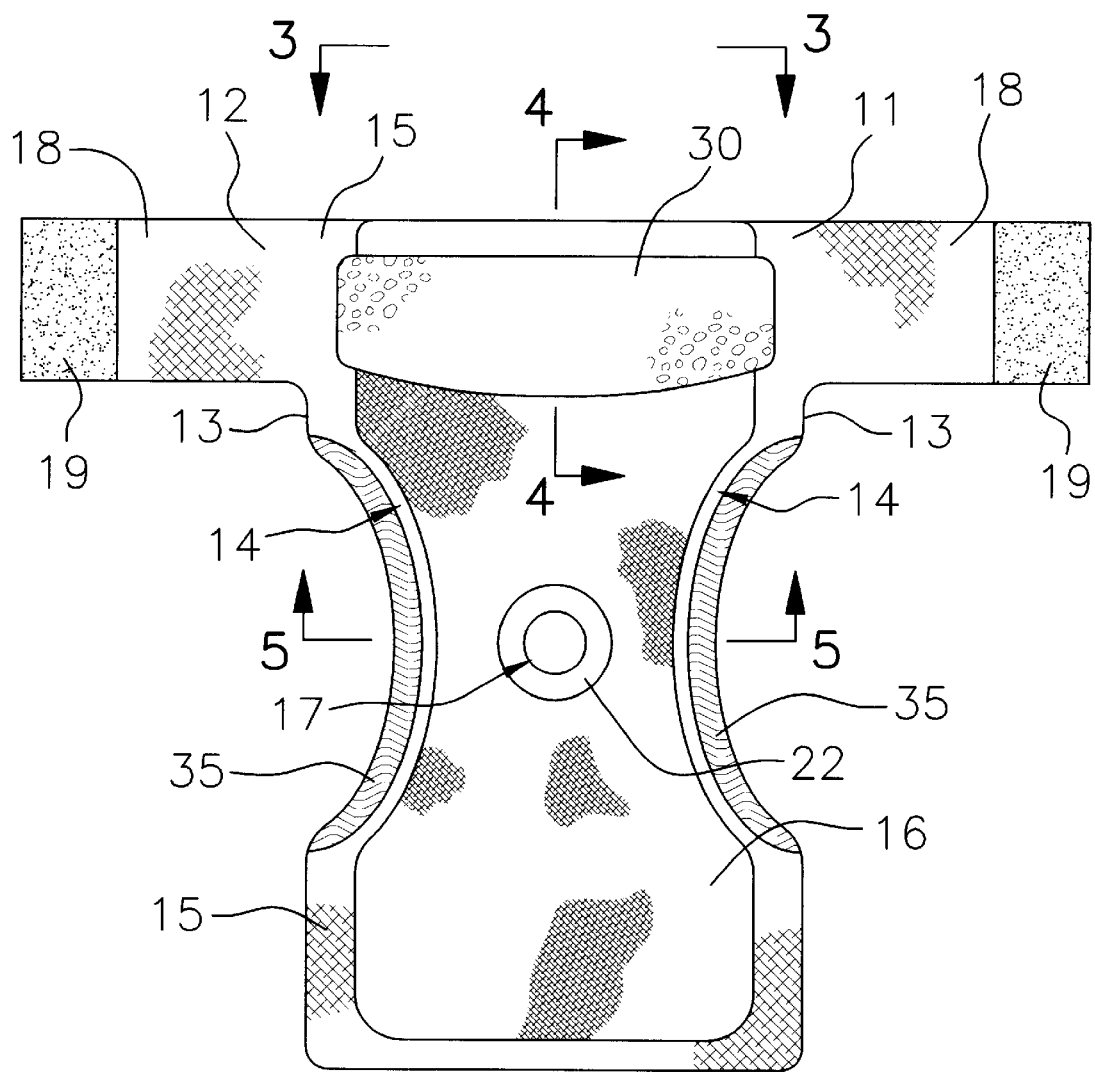
FIG. 2 is a top plan view of the diaper member of the present invention.
Figure 3:
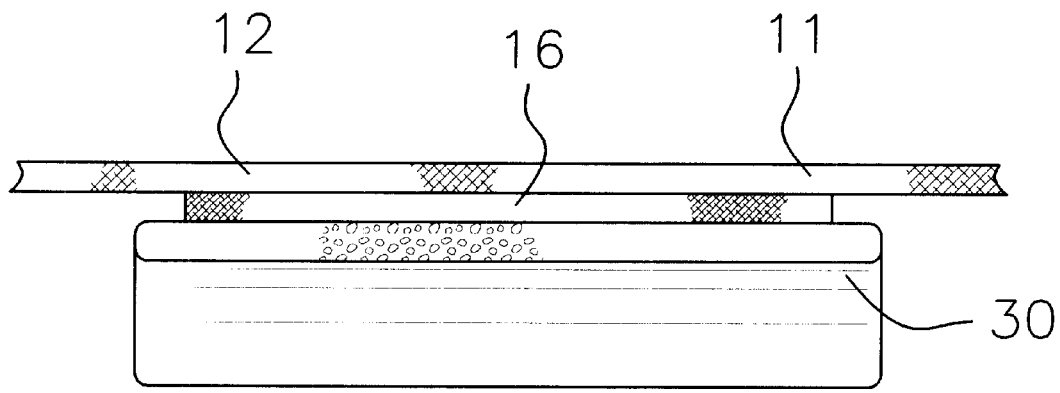
FIG. 3 is a partial top edge view of the diaper member of the present invention.
Figure 4:
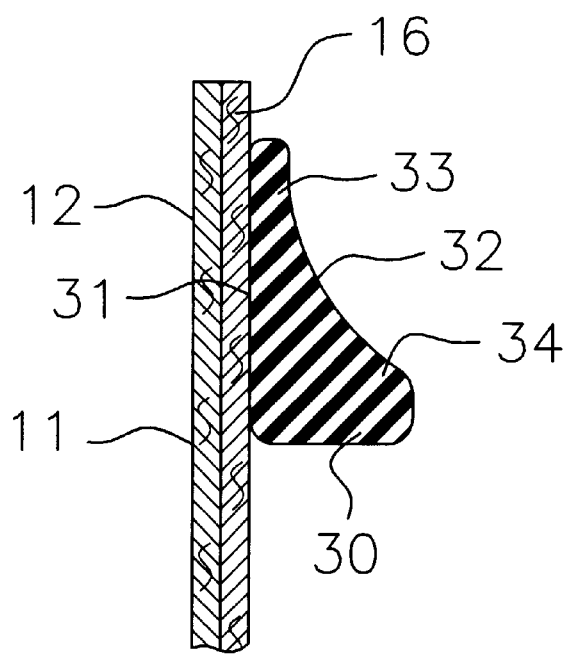
FIG. 4 is a partial cross-sectional view of the diaper member and the diaper lift member of the present invention.
Figure 5:
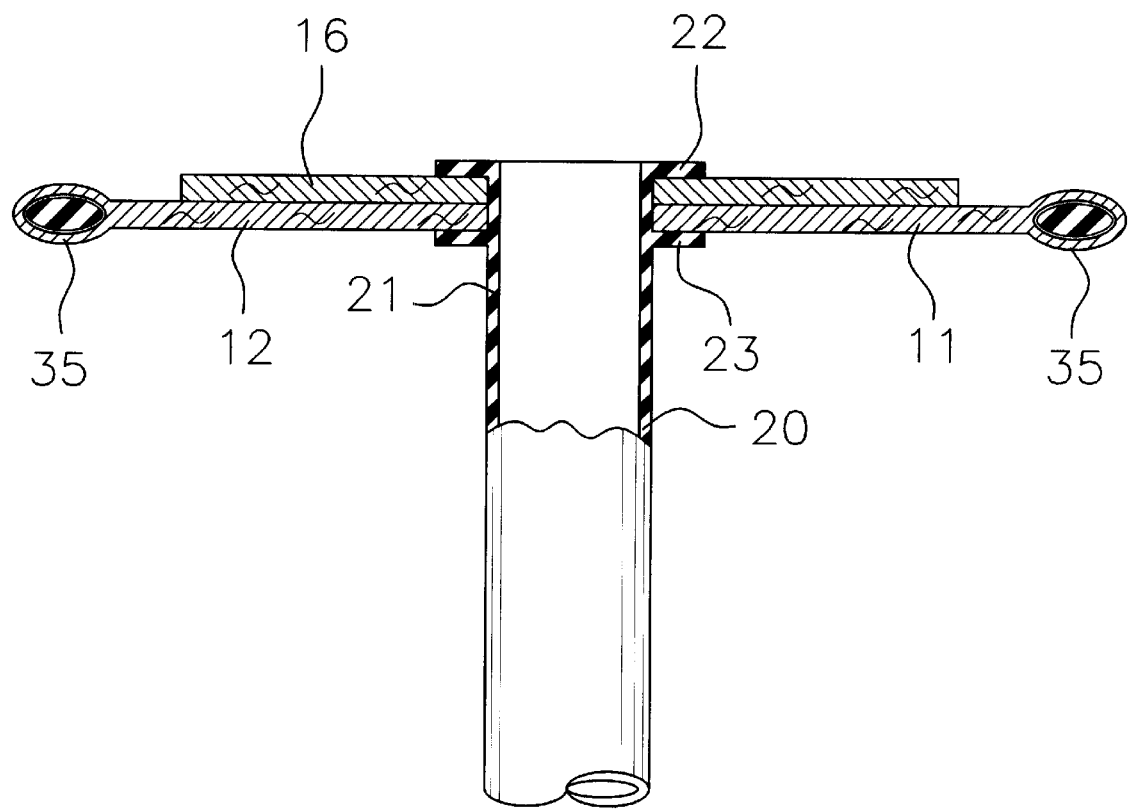
FIG. 5 is a cross-sectional view of the diaper member of the present invention.

With reference now to the drawings, and in particular to FIGS. 1 through 5 thereof, a new incontinence diaper and receptacle apparatus embodying the principles and concepts of the present invention and generally designated by the reference numeral 10 will be described.

As best illustrated in FIGS. 1 through 5, the incontinence diaper and receptacle apparatus 10 generally comprises a diaper member 11 which includes a sheet of material 12 and at least one inner absorbent liner 16 being conventionally attached to a side of the sheet of material 11. The sheet of material 11 includes side edges 13 having inwardly-curved leg-receiving portions 14, and also includes end portions 15. The diaper member 11 further includes flexible leak-proof strips of material 35 being conventionally attached along the inwardly-curved leg-receiving portions 14 to prevent bodily waste fluids from leaking out of the diaper member 11. The diaper member 11 also includes a hole 20 being centrally-disposed through the sheet of material 12 and the at least one inner absorbent liner 16.

Means for fastening the diaper member 11 about a person's midsection includes flexible tab members 18 integrally extending outwardly from the side edges 13 at one of the end portions 15 of the sheet of material 12 and being fastenable to the sheet of material 12 about the person's midsection, and also includes adhesive 19 being disposed upon end portions of the tab members 18 so that the tab members 18 fasten to the sheet of material 12.

A hose 20 is in fluid communication with the diaper member 11, and includes annular flange portions 22, 23 being spaced apart and being conventionally attached about a first end portion 21 of the hose 20 and being engaged about an edge of the hole 17 of the diaper member 11 to securely attach the hose 20 to the diaper member 11, and also includes a cap-like fastener 25 being conventionally attached about a second end portion 24 of the hose 20.

A container 26 is conventionally connected to the hose 20 for receiving a person's bodily waste. The container 26 includes calibrated markings 27 displayed upon a side wall thereof to effectively monitor the person's bodily waste, and also includes a lid 28 having an opening 29 therein. The cap-like fastener 25 is detachably attached to the lid 28 and being in fluid communication with the container 26.

A diaper lift member 30 is conventionally attached to the diaper member 11 for lifting the diaper member 11 about a person's midsection to facilitate flow of the person's waste through the hose 20. The diaper lift member 30 is attached to an inner side of one of the end portions 15 of the diaper member 11, and includes a pliable elongate body being laterally extended upon the diaper member 11 and having a flat side 31 which is attached flush to the diaper member 11 and also having an opposed side 32 which is generally beveled with the diaper lift member 30 having an upper portion 33 and an enlarged lower portion 34 for engaging about a person's midsection to facilitate drainage of the person's bodily waste through the hole 17 with the hole 17 being disposed at a lowermost portion of the diaper member 11. The pliable elongate body is generally made of foam rubber.

In use, the user wraps the diaper member 11 about one's midsection and fastens the tab members 18 to the diaper member 11 to effectively secure the diaper member 11 with the diaper lift member 30 being pressed against the user's midsection to effectively hold the diaper member 11 about the user's midsection so that the hole 17 is positioned at the bottommost point of the diaper member 11 so that the user's bodily waste will empty through the hole 17 into the container 26.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the arts and all equivalent relationships to those illustrated in the drawings and described in the specification are intended to be encompassed by the present invention.

Therefore, the foregoing is considered as illustrative only of the principles of the incontinence diaper and receptacle apparatus. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An incontinence diaper and receptacle apparatus comprising:

a diaper member which includes a sheet of material and at least one inner absorbent liner being attached to said sheet of material, said sheet of material including side edges having inwardly-curved leg-receiving portions, and also including end portions;

means for fastening said diaper member about a person's midsection;

a hose being in fluid communication with said diaper member;

a container being connected to said hose for receiving a person's bodily waste; and a diaper lift member being attached to said diaper member for lifting said diaper member about the person's midsection to facilitate flow of the person's waste through said hose, said diaper lift member being attached to an inner side of one of said end portions of said diaper member, and including a pliable elongate body being laterally extended upon said diaper member and having a flat side which is attached to said diaper member and also having an opposed side which is generally beveled with said diaper lift member having an upper portion and an enlarged lower portion for facilitating drainage of the person's bodily waste through said hole such that said hole is disposed at a lowermost portion of said diaper member.

2. An incontinence diaper and receptacle apparatus as described in claim 1, wherein said pliable elongate body is generally made of foam rubber.

* * * * *